United States Patent [19]

Bayerlein et al.

[11] Patent Number: 5,007,688
[45] Date of Patent: Apr. 16, 1991

[54] MOBILE INTENSIVE CARE UNIT

[75] Inventors: Jörg Bayerlein; Eric Hecker; Peter Hoeck, all of Stockelsdorf, Fed. Rep. of Germany; Francesco Milani, Giubiasco, Switzerland

[73] Assignee: Drägerwerk Aktiengesellschaft, Lübeck, Fed. Rep. of Germany

[21] Appl. No.: 337,669

[22] Filed: Apr. 13, 1989

[30] Foreign Application Priority Data

May 5, 1988 [DE] Fed. Rep. of Germany ....... 3815273

[51] Int. Cl.$^5$ .............................................. A47B 81/00
[52] U.S. Cl. ...................................... 312/7.2; 312/209
[58] Field of Search ................. 312/209, 234, 7.2, 107

[56] References Cited

U.S. PATENT DOCUMENTS

| | | | |
|---|---|---|---|
| 656,556 | 8/1900 | Lind | 312/209 |
| 727,166 | 5/1903 | Harrison et al. | 312/209 |
| 727,166 | 5/1903 | Harrison | 312/234 |
| 2,307,992 | 1/1943 | Calhoun et al. | 312/234 X |
| 3,229,368 | 1/1966 | Tocchini | 312/209 X |
| 3,969,006 | 7/1976 | Brown | 312/209 X |
| 4,848,855 | 7/1989 | Cone | 312/107 |

*Primary Examiner*—Joseph Falk
*Attorney, Agent, or Firm*—McGlew and Tuttle

[57] ABSTRACT

A mobile intensive care unit for the reception of devices and instruments, which are arranged in various sections of a frame, is improved so that an ergonomically coordinated arrangement of the devices is possible, allowing for a combined use and control from an operating level for the parameters to be set and controlled, and also allowing for uninhibited access to the various sections. For this purpose the sections, which are inclined away from the vertical plane at several different angles, are superimposed in connected levels; in an upper section, a middle section, and a lower section for the reception and use of the devices. The upper section has a viewing and indicator unit which is approximately vertical, the section below it comprises control and indicator elements for a setting and control unit and the lower section, which is approximately horizontal, comprises an inclined reception holder for liquid dosing units and it comprises at least one approximately horizontal depositing surface for the desk holder.

11 Claims, 3 Drawing Sheets

MOBILE INTENSIVE CARE UNIT

BACKGROUND OF THE INVENTION

Field of the Invention

The invention relates, in general, to emergency medical treatment devices and, in particular, to a new and useful mobile intensive care and treatment unit for the reception of devices and instruments, which are received by a frame divided into several sections.

A similar intensive care unit is known from German patent No. 29 44 492.

The known unit has a wheel frame having several drawers or cupboards on the lowest level, above which a carrying area or table is arranged in table height. A vertical frame is mounted to the back of the cupboard, carrying several superimposed boards. The various locations for depositing, i.e. depositing surfaces of the intensive care unit serve for the depositing or mounting of various devices depending on the requirements: such as a respirator, respiration monitors and control units or dosing devices for the dosing of narcotics. The arrangement of the various devices and their operation is determined by the given depositing space, so that the operator of the mobile intensive care unit faces an ergonomically unfavorable situation. Each of the devices has to be operated on its own, each of the devices having its own operation directions. The constant change of operation levels and the kinds of operation makes the handling of the devices appointed to the unit complex and complicated and therefore holds the danger of incorrect operation or a diagnostic error by the treating doctor or nurse. As the various devices are connected to one another by means of signal lines or also medium lines, such as air pressure lines or liquid dosing lines, the non-integrated arrangement of the lines inhibits the operation.

SUMMARY OF THE INVENTION

Therefore the present invention provides an improved mobile intensive care unit providing an ergonomically connected arrangement of the devices, which allows for a combined operation and control from one operation level for the parameters to be set and controlled, and also for the clear and uninhibited access to the various sections.

According to the invention, sections of the device are arranged in several connected and superimposed areas which are arranged at various angles away from a vertical plane and which serve for the reception and the operation of the devices. Herein the uppermost section is substantially vertical and serves as a viewing and indicator unit, the section below comprises operation and indicator elements for a setting and control unit, the section below this, which is approximately horizontal, has essentially a desk-shaped holder section for liquid-dosing units and an at least approximately horizontal deposit surface.

The advantages achieved by the invention are contained in the fact that several levels are arranged according to the criterium of frequency of use: the uppermost viewing and indicator panel is arranged advantageously in the view of the user and can be checked by him with one look. The operation section, which is the middle section, takes into account a desirable fast and easy operation of the required setting elements. The holder for the dosing units below guarantees that their frequent change can be effected easily and safely and that possible leakages or spills of dosing liquid do not lead to the soiling of operating or setting elements, as they are all arranged above the desk-shaped holder.

The operation of a multitude of separate devices with their respective setting regulations is no longer required, now each of the devices is connected to the combined setting and control unit by means of their respective signal or control lines, setting and control unit having a uniform operation pattern for all of the devices. A simplification can be achieved if the setting and control unit has a micro-processor or micro-computer processing the setting and control parameters, which makes the various parameters to be indicated available in a form advantageous for the user and uniform for all devices.

Advantageously infusion holders and the respective infusion pumps can be provided as dosing units next to the section for the viewing and indicator unit. Thus the infusion pumps required for volume balancing are placed in the vicinity of the liquid dosing units, which can e.g. be syringe pumps, to arrange the tubes as clearly as possible.

The arrangement of infusion syringe pumps in the desk-shaped holder is advantageous because a frequent change of syringes, which can take place several times per hour, can be effected easily, and a necessary change of the liquid duct line is effected without problems.

In many cases it is necessary to install a measuring amplifier for the reception of various patient parameters, whose measuring signals have to be processed in the setting and control unit and indicated on the viewing and indicator unit. Among these are e.g. electrocardiogram, or blood pressure monitors, or meters measuring the blood-gas saturation. To avoid that these additional measuring amplifiers destroy the ergonomically uniform structure, it is advantageous to provide the wheel frame with an extension arm. Herein the measuring amplifiers can be held and their signal lines can be led easily into the setting and control unit as additional ducts. As the intensive care unit is usually located at the head of the patient'bed and therefore at the wall of the patient's room, the lines of the measuring sensors to the patient are very short when the measuring amplifiers are arranged on a lateral arm and the arm can even be inserted between the head of the patient's bed and the wall.

To be able to arrange the measuring amplifiers on the right side of the intensive care station as well as on the left side without any cumbersome rearrangement of the devices, a hollow compartment is arranged on the back of the wheel frame, through which the arm can be slid from one side to the other. During the transport of the intensive care unit the arm can be left in the compartment to prevent it from damage.

Advantageously a respirator can be arranged below the approximately horizontal section and be connected to the setting and control unit in the operating section. Therefore it is possible to centralize even the adjustment possibilities of a respirator and to make them controllable at the setting and control unit and visible on the viewing and indicator unit. Herein the respirator can even be located in more remote parts without encumbering its operability. The arrangement of the respirator in the lowest location has the added advantage that condensed water possibly collecting in the respirator tube is automatically returned to the humidifier of the respirator or is removed in another adequate way, so that the patient receiving artificial respiration is kept free of condensed water.

For a better protocolling of the activities an extendable writing and depositing surface is arranged under the central operating or control unit, which receives protocol papers in the inserted position and which has an optimal height for writing and for leaning an arm on it during extensive operation of the central control unit in the extended position.

Accordingly, it is an object of the invention to provide an improved device for use in hospitals particularly in intensive care units which comprises a wheeled frame which may be moved from place to place and which includes a lower or base portion which advantageously carries a respirator having a flat surface which receives an obliquely extending desk carrying one or more syringes thereon. The device also includes a middle section or intermediate part which has a slightly inclined front surface having a viewing portion for observing, controlling and indicating elements and an upper portion which includes a substantially vertical viewing and indicating unit.

A further object of the invention is to provide a mobile intensive care device which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which a preferred embodiments of the invention is illustrated.

DETAILED DESCRIPTION OF THE PREFERRED EMBODIMENT

Figure 2:
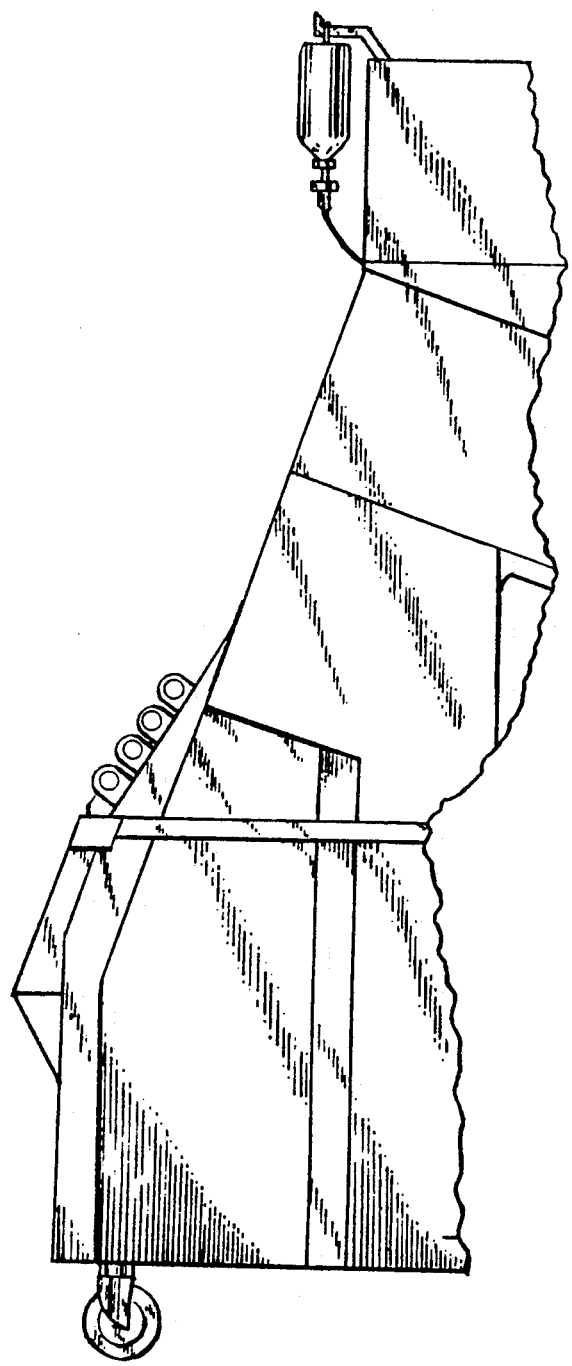
FIG. 2 is a side view of the intensive care unit in accordance with the invention.

Referring to the drawings, in particular, the invention embodied therein comprises a device for use in hospitals comprising a mobile intensive care unit which includes a wheeled frame 1 which in the embodiment indicated has three separate main portions which in the embodiment illustrated includes a lower portion 44, an intermediate portion 33 above the lower portion and an upper portion 22 which is above the intermediate portion 3. Lower portion 44 also has a compartment 19 with rails 20 for the slidable motion of an arm 16 which may be projected out of the other side of the device (see FIGS. 2 and 3).

Figure 1:
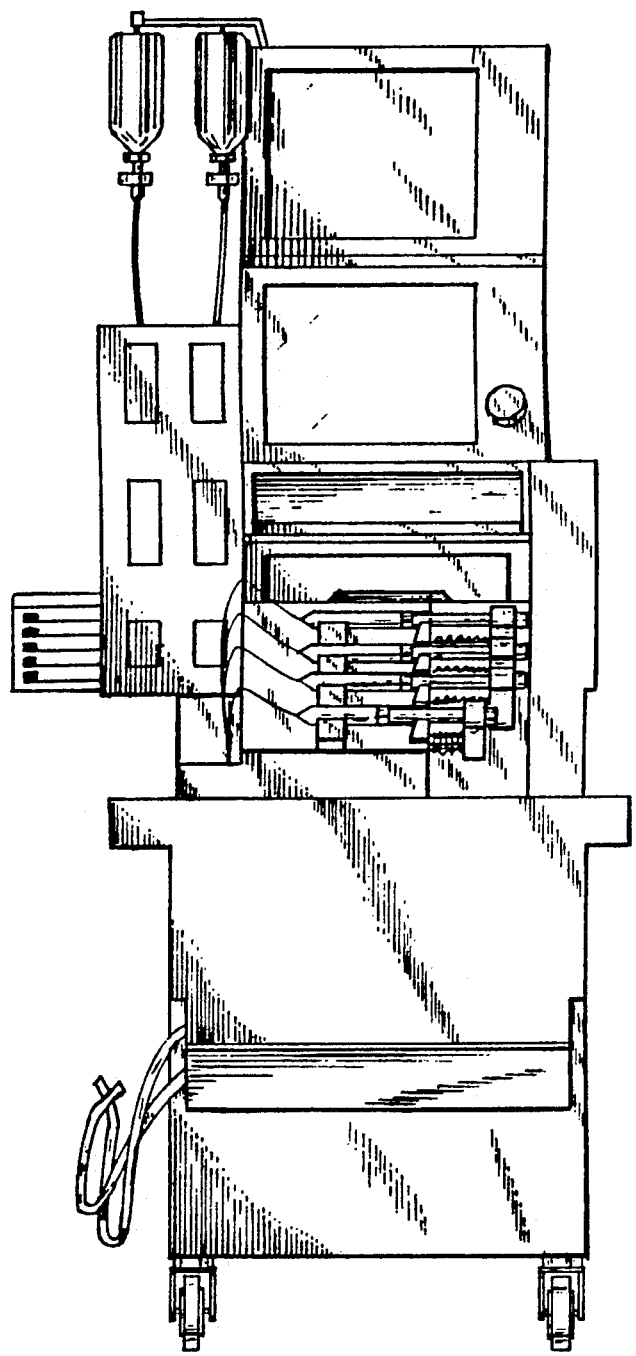
FIG. 1 is a front view of an intensive care unit in accordance with the invention.
Figure 3:
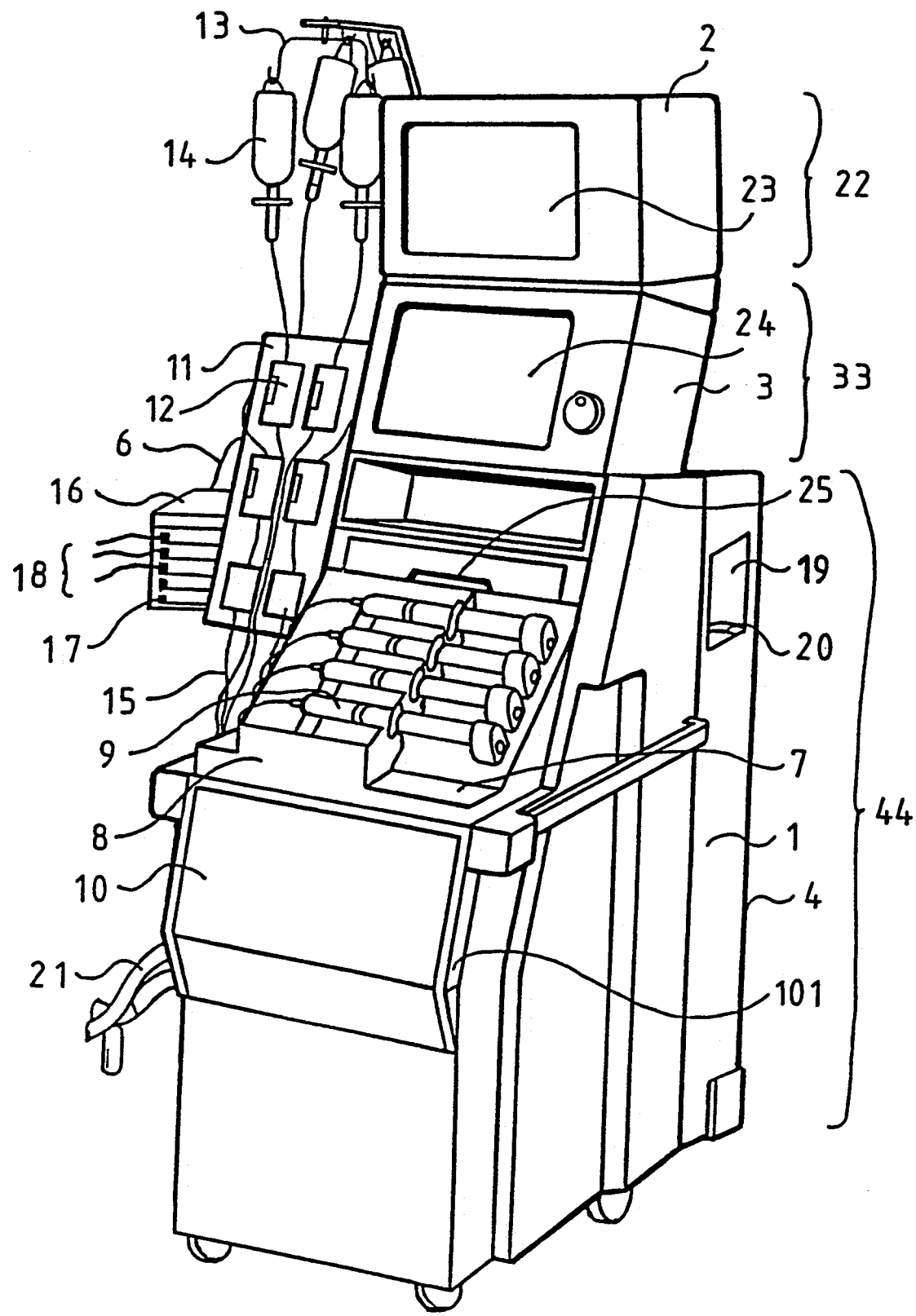
FIG. 3 is a front top perspective view of an intensive care unit constructed in accordance with the invention.

FIG. 3 shows an intensive care unit on a wheel frame 1 comprising the various sections with the respective devices. The top section shows a viewing and indicator unit 2 for the representation of the parameters and other data read by the devices and chosen by the user in the setting and control unit 3 below. A computer-assisted processing unit 4 is provided below the setting and control unit inside the wheel frame 1, which receives all signal and control lines 6 on its back (not visible). The signals processed in it are fed into the setting and control unit 3 and represented on the viewing and indicator unit 2 or on the setting and control unit 3 depending on the user's requirements. An area of a depositing surface or section 7 on the frame 1 which is nearly horizontal or leaning toward the horizontal plane has an essentially desk-shaped holder 8 for one or several liquid dosing units, e.g., for infusion syringe pumps 9. A respirator 10 is suspended in a cabinet or housing 101 below the section 7 and the holder 8, whose control elements can also be controlled from the setting and control unit 3 (see FIG. 3). A receiver block 11 which can hold several infusion pumps 12, is fastened to the left of the setting and control unit 3. The pumps 12 are fed by the infusion liquid bottles 14 hanging over them from stands 13 and the infusion liquid is led to a patient (not shown) by infusion lines 15. An extension arm 16, arranged laterally with regard to the wheel frame 1, carries several measuring amplifiers 17 as inserts (see FIGS. 1 and 3). Their measuring lines 18 are also led to the patient. A hollow compartment 19 provided at the back of the wheel frame 1 contains rails 20, on which the extension arm 16 can be slid through and fastened on the other side of the wheel frame 1. Respiration tubes 21 from the respirator 10 also lead to the patient. The respirator 10 is mounted advantageously on telescopic rails, so that it can be moved out of its receiving housing 101 and the connected pneumatic and electrical supply lines are freely accessible and so that a change of devices is easy.

In the overall arrangement of the various devices in the wheel frame 1 care was taken that the upper section 22 is as vertical as possible to allow for easy reading in the eye-height of the user. The middle section 33 with its setting and control unit 3 and its controlling and indicating elements 24 have a user-friendly height and are inclined backward from the vertical plane, so that a favorable reach and operating position for a standing user is provided. The desk-shaped holder 8 obliquely extending on the essentially horizontal level 7 allows for an especially easy handling of the infusion syringe pumps 9, which are located nearby even when the user is sitting.

Below the controlling and indicator elements 24 a desk-extension leaf 25 for writing and depositing is provided. In its inserted position it retains the protocol papers. In extended position it forms a support for writing and for the arm during longer use of the control elements.

While a specific embodiment of the invention has been shown and described in detail to illustrate the application of the principals of the invention, it will be understood that the invention may be embodied otherwise without departing from such principles.

What is claimed is:

1. A mobile intensive care unit for the reception of devices and instruments, comprising: a lower section mounted on roller means for movement of the unit, said lower section defining a compartment and including an upper surface defining a horizontal depositing surface; an intermediate section arranged above said lower section, said intermediate section defining an inclined surface extending from said depositing surface upwardly and rearwardly, said inclined surface including liquid dosing unit receiving elements for receiving liquid dosing units, said liquid dosing receiving elements being provided at spaced locations, said liquid dosing receiving elements releasably holding liquid dosing elements and cooperating to form an array of liquid dosing elements; an intermediate section positioned above and behind said inclined surface, said intermediate section including a setting and control unit; and an upper section positioned substantially vertically above said intermediate section, said upper section including a viewing and indicator unit; and, an extension arm mounted on said lower portion, said extension arm extending outwardly on one side of said unit, said extension arm is supported on tracks within a hollow compartment formed in said lower section, said hollow compartment and tracks extending through said lower section such that said extension arm may be positioned on either a first side or a second side of said lower section.

2. An intensive care unit according to claim 1, including an infusion holder arranged alongside said upper section, a receiver back alongside said intermediate portion containing a plurality of infusion pumps for said infusion holders, said infusion holders having infusing elements with line connectable to said infusion pumps.

3. An intensive care unit according to claim 1, including a plurality of infusion syringe pumps arranged on said desk holder.

4. An intensive care unit according to claim 3, including an extension arm mounted on said lower portion, said arm extending outwardly on one side of said unit and including a measurement amplifier carried by said arm and connected to said intermediate section for transfer of measuring signals to said setting and control unit.

5. An intensive care unit according to claim 4, wherein said extension arm has a portion slidable transversely on said lower section, said lower section having a transversely extending slot with a guide rail therein on which said arm is movable.

6. An intensive care unit according to claim 5, including a respirator in said lower section arranged below said desk holder and connected to said setting and control unit.

7. An intensive care unit according to claim 6, including a connection between said setting and control unit and said viewing and indicator unit of said upper section, said desk having a plurality of liquid dosing units, said dosing units being connectable to said infusion pumps, said arm containing a measuring amplifier which is connectable to said pumps.

8. A mobile intensive care unit according to claim 6, including a connection between said setting and control unit and said viewing and indicator unit of said upper section, said desk having a plurality of liquid dosing units, said dosing units being connectable to said infusion pumps, said arm containing a measuring amplifier which is connectable to said pumps.

9. A mobile intensive care unit for the reception of devices and instruments which are arranged in various sections, comprising a lower section having a lower respirator receiving cabinet, a respirator in said cabinet having respirator tubes extending out of said cabinet to one side of said lower section, said lower section having a desk above said respirator cabinet, an inclined desk surface on said desk, a plurality of syringe pumps carried on said inclined surface, said lower section having a transversely extending slot therethrough with an arm rail extending along said slot, an arm slidable on said slot and extendable out of one side of said lower section, a plurality of measuring lines carried by said arm, a receiver block on one side of said lower section having a plurality of infusion pumps thereon, a middle section extending above said lower section and having an inclined face with controlling and indicating elements and said middle section also having setting and control units, and a vertical upper section above said intermediate section having a viewing and indicating face which extends substantially vertically, a stand extending outwardly from the upper section and carrying a plurality of infusion fluid supply bottles with lines extending to respective infusion pumps on said receiver block, said setting and control unit comprising a computer-aided processing unit to which all signal and control lines of the devices are lead as input channels, said computer-aided processing unit processing all information collectable from said channels, so that they are directly available on said viewing and indicating unit and on said indicator section of said setting and control unit in a form of representation uniform for all devices.

10. An intensive care unit according to claim 8, wherein there is an extendible desk extension leaf in said lower section extending outwardly above said desk providing means for writing and depositing thereon and for retaining protocol papers thereon.

11. A mobile intensive care unit for the reception of devices and instruments, comprising: a lower section mounted on roller means for movement of the unit, said lower section defining a compartment and including an upper surface defining a horizontal depositing surface; an intermediate section arranged above said lower section, said intermediate section defining an inclined surface extending from said depositing surface upwardly and rearwardly, said inclined surface including liquid dosing unit receiving elements for receiving liquid dosing units, said liquid dosing receiving elements being provided at spaced locations, said liquid dosing receiving elements releasably holding liquid dosing elements and cooperating to form an array of liquid dosing elements; an intermediate section positioned above and behind said inclined surface, said intermediate section including a setting and control unit; and an upper section positioned substantially vertically above said intermediate section, said upper section including a viewing and indicator unit; and, an extension arm mounted on said lower portion, said extension arm extending outwardly on one side of said unit, said extension arm including a measure and amplifier carried by said arm, said measurement amplifier connected to said intermediate section for transfer of measuring signals to said setting and control unit.

* * * * *